US012597515B2

(12) United States Patent
Koga

(10) Patent No.: US 12,597,515 B2
(45) Date of Patent: Apr. 7, 2026

(54) HEALTH MANAGEMENT AND GUIDANCE INSTRUCTION ISSUANCE ASSISTANCE

(71) Applicant: KOGA SOFTWARE CO., LTD., Tokyo (JP)

(72) Inventor: Shoji Koga, Tokyo (JP)

(73) Assignee: Koga Software Co., Ltd., Tokyo (JP)

( * ) Notice: Subject to any disclaimer, the term of this patent is extended or adjusted under 35 U.S.C. 154(b) by 143 days.

(21) Appl. No.: 17/843,044

(22) Filed: Jun. 17, 2022

(65) Prior Publication Data

US 2023/0411000 A1    Dec. 21, 2023

(51) Int. Cl.
*G16H 40/67* (2018.01)
*G16H 20/30* (2018.01)
*G16H 20/60* (2018.01)

(52) U.S. Cl.
CPC ............. *G16H 40/67* (2018.01); *G16H 20/30* (2018.01); *G16H 20/60* (2018.01)

(58) Field of Classification Search
CPC ........ G16H 40/67; G16H 20/30; G16H 50/20; G16H 50/30; G16H 20/60; G16H 15/00; G16H 80/00; G16H 20/00
See application file for complete search history.

(56) References Cited

U.S. PATENT DOCUMENTS

2002/0194022 A1* 12/2002 Comite ................. G16H 40/20
                                                        705/2
2003/0208108 A1* 11/2003 Shewmake ............ G16H 70/20
                                                        128/920

2018/0301209 A1* 10/2018 Kim ...................... G16H 20/10
2019/0344080 A1* 11/2019 McDonald .............. A61B 5/24
2021/0233656 A1* 7/2021 Tran ...................... G16H 20/30

FOREIGN PATENT DOCUMENTS

JP          2021167987 A     10/2021

OTHER PUBLICATIONS

Stut W, Deighan C, Armitage W, Clark M, Cleland JG, Jaarsma T. Design and Usage of the HeartCycle Education and Coaching Program for Patients With Heart Failure. JMIR Res Protoc. Dec. 11, 2014;3(4): e72. doi: 10.2196/resprot.3411. PMID: 25499976; PMCID: PMC4275507 (Year: 2014).*

* cited by examiner

*Primary Examiner* — Joseph D Burgess
(74) *Attorney, Agent, or Firm* — Ogilvie Law Firm

(57)                     ABSTRACT

A purpose is to provide a health management system that can support the health of each patient safely and continuously by collaborating with exercise and nutrition specialists. In a health management system, a service providing server, a doctor server, and a client terminal share information data via a network. The client terminal is provided with an identification information registration means, a medical interview information registration means, and an information transmission means. The service providing server is provided with a guidance instruction issuance request means for transmitting an issuance request for guidance instruction data regarding exercise prescription and nutrition prescription by a doctor to the doctor server. The doctor server is provided with a guidance instruction automatic creation means, a guidance instruction manual correction means, and a guidance instruction issuance means based on the information data obtained from the guidance instruction issuance request means.

20 Claims, 11 Drawing Sheets

COMPUTING SYSTEM 102, 202 OF MACHINES 101

MEMORY / MEDIA 112    KERNEL 120    TOOLS 122    USER INTERFACE 124

PROCESSOR(S) 110    DISPLAY(S) 126    OTHER HARDWARE 128

CONFIGURED MEDIUM 114

INSTRUCTIONS 116

DATA 118

CLOUD 130

103

USER(S) 104

NETWORK(S) 108

PERIPHERAL(S) 106

HEALTH MANAGEMENT AND GUIDANCE INSTRUCTION ISSUANCE ASSISTANCE

TECHNICAL FIELD

The present invention relates to techniques for giving advice on exercise and nutrition to a user and managing a health condition under the guidance of one or more specialists.

BACKGROUND

In recent years, people's awareness of health has increased, and in particular, many people are actively exercising for the purpose of preventing or improving metabolic syndrome. Here, metabolic syndrome refers to a state in which any two or more of hyperglycemia, hypertension, and lipid abnormality are combined in addition to visceral fat obesity, and is called visceral fat syndrome.

Also, recently, people are also becoming more aware of the prevention and improvement of locomotive syndrome, which is at high risk of requiring long-term care due to motor dysfunction.

In order to prevent and improve metabolic syndrome and locomotive syndrome, it is necessary to exercise according to the person. Therefore, the present inventor has already proposed an exercise program automatic creation system capable of taking in blood information, predicting lifestyle-related diseases, and automatically creating an exercise program (Refer to Patent Document 1.). According to the exercise program automatic creation system of Patent Document 1, it is possible to automatically create the exercise program based on medical evidence.

However, in the exercise program automatic creation system of Patent Document 1, the user can easily create the exercise program, but cannot continuously receive advice from specialists such as doctors and dietitians. For that reason, there is a problem that it is difficult to continue to exercise and improve lifestyle.

Patients who need to exercise and improve their lifestyle need to continue to exercise and improve their diet for a long period of time, and it is desirable to change the training content and diet menu according to changes in their health condition. And it is also important from the viewpoint of safety that such menu changes should be made according to the individual health condition of the patient based on the advice of exercise and nutrition specialists who have specialized knowledge.

Also, exercise, nutrition and medical care are not considered separately, for example, nutritional status should be considered when deciding on an exercise menu, and it is necessary to consider what kind of exercise to perform when calculating the required calorie intake. In addition, when a patient has a chronic disease, a medical viewpoint is indispensable for creating an exercise menu and a meal menu. In other words, in order to exercise and improve lifestyle of the patient, it is necessary for doctors and specialists in exercise and nutrition to work together to continuously support the patient.

As a technology that enables users to share information by linking doctors and exercise/nutrition specialists via a network, a health care system is known that allows users to search for exercise facilities, doctors, medical institutions affiliated with them, etc. from their own terminals via a network (Refer to Patent Document 2.). This not only makes it possible to search for exercise facilities and medical institutions, but also improves convenience by registering and sharing information about patients in a database.

The health care system disclosed in Patent Document 2 aims at network-type medical care in which specialists such as doctors and dietitians collaborate. However, it is not enough disclosure about how to communicate between patients and specialists, or between specialists, and it is insufficient as a system for each specialist to work together to exercise and improve lifestyle of patients.

In addition, the exercise therapy prescription issued by the doctor and the exercise program created by the exercise facility are all created by human hands, and there is a problem that they are complicated.

PATENT DOCUMENTS

[Patent Document 1] JP2016-119006A
[Patent Document 2] JP2002-358371A

DETAILED DESCRIPTION

In view of such circumstances, it is an object of the present invention to provide a health management system in which specialists in exercise and nutrition can work together to safely and continuously support the health of each patient. It is also an object of the present invention to provide a device capable of safely and smoothly prescribing exercise and nutrition by a specialist doctor in the health management system.

To solve the above problems, in the health management system, a service providing server, a doctor server, and a client terminal share information data via a network. The client terminal is provided with an identification information registration means for inputting identification information data of users who receive services, a medical interview information registration means for inputting medical interview information data, and an information transmission means for transmitting the input identification information data and medical interview information data to the service providing server. And the service providing server is provided with a guidance instruction issuance request means for creating an issuance request data of guidance instruction regarding exercise prescription and nutrition prescription by a doctor based on the identification information data and the medical interview information data, and transmitting the issuance request data to the doctor server. The doctor server is provided with a guidance instruction automatic creation means for automatically creating guidance instruction data, a guidance instruction manual correction means for the doctor to modify the automatically created guidance instruction data, and a guidance instruction issuance means for transmitting guidance instruction data checked by a doctor to the service providing server and client terminal, based on the issuance request data obtained from the guidance instruction issuance request means.

With the above configuration, all processing from user registration to issuance of the guidance instruction can be performed on the Web, so it can be used as a highly convenient system.

The doctor here is a doctor who has specialized knowledge about lifestyle-related diseases, metabolic syndrome, locomotive syndrome, etc. And the doctor server is a server computer that can be accessed by specialist doctors.

The guidance instruction is a written or electronic file that describes the exercise prescription and nutritional prescription by the doctor. Therefore, in this specification, the guidance instruction is also used in the sense of referring to the guidance instruction data. In the present invention, the guidance instruction is created as an electronic file, but it is possible not only to send and receive as data but also to send a printed document.

By automatically creating the guidance instruction data, it is possible to issue the guidance instruction quickly and easily. In addition, by providing the guidance instruction manual correction means, the doctor can check the guidance instruction data.

The user's identification information data is a name, an email address, etc., and may include gender, date of birth, weight, height, body fat mass, and the like. Further, it is preferable that the medical interview information data includes not only the medical interview related to the lifestyle but also the information related to the medical examination result. Information such as gender, date of birth, weight, height, and body fat mass may be included in the medical interview information data. The medical interview is not limited to answering a question with yes/no, but may be answered in text.

In the health management system of the present invention, it is preferable that the service providing server further includes an interview information registration means for inputting interview information data based on the interview result between an exercise or nutrition specialist and a user. It is also preferable that the information transmission means further is used to send the interview information data to the doctor server, and that the guidance instruction manual correction means in the doctor server uses the received interview information data to correct the guidance instruction data.

An exercise specialist is, for example, a health exercise instructor, and a nutrition specialist is, for example, a dietitian or a registered dietitian. It is preferable that the interviews between the user and the above specialists are performed by video call using the Internet, but the present invention is not limited to this, and the interview may be conducted by actually meeting, or voice call, as simple methods. The interview will be conducted between at least one of the exercise and nutrition specialist and the user, but may be attended by both the exercise and nutrition specialists. In addition, a plurality of exercise specialists and a plurality of nutrition specialists may participate.

The interview information data is not used in the guidance instruction automatic creation means, but it can be referred to when the doctor corrects the guidance instruction data by the guidance instruction manual correction means.

Interviews between the user and the above specialists are not essential for issuing the guidance instruction, but by conducting interviews, the doctor can grasp the user's health condition in detail, which is more accurate and effective. Therefore, it is possible to create more accurate and effective guidance instruction.

The health management system of the present invention further includes a means for selecting a health improvement course tailored to the user, and it is preferable that the guidance instruction automatic creation means automatically creates the guidance instruction data based on identification information data, medical interview information data, and a selected health improvement course.

As a health improvement course, for example, it is conceivable that a course such as a "lifestyle-related disease improvement course" or a "sarcopenia course" can be selected. Sarcopenia refers to the loss of muscle mass due to aging or disease, and the sarcopenia course is a course aimed at preventing such loss of muscle mass or increasing muscle mass. The course selection is preferably made by an exercise or nutrition specialist, but may be configured to be user selectable, for example.

In the health management system of the present invention, it is preferable that the service providing server further includes an exercise program automatic creation means for automatically creating an exercise program based on the guidance instruction data received from the doctor server and an exercise program manual correction means for making manual corrections as needed.

By automatically creating the exercise program, the burden on health exercise instructors and the like involved in creating the exercise program is reduced. Further, by providing the exercise program manual correction means, the exercise program can be made more suitable for the user.

The health management system of the present invention further includes a wearable terminal that is connected to a network and can transmit and receive data, and the wearable terminal is provided with a biometric information acquisition means for acquiring user biometric information data including pulse rate and step count. By providing such a configuration, it is preferable that the information data can be shared among the service providing server, the doctor server and the client terminal through the network.

Daily vital data is required for specialists to instruct users online based on the guidance instruction. Therefore, by equipping the wearable terminal, daily biometric information can be acquired and more effective guidance can be provided. Here, the biological information data is a pulse rate, a heart rate, a respiratory rate, a body temperature, a step count, a moving distance, a floor number, a calorie consumption, and the like. Further, the shape of the wearable terminal is not particularly limited, and a wristwatch type, a glasses type, a wristband type, a sock type, and the like are widely included.

In the health management system of the present invention, it is preferable that the service providing server and the doctor server further provide an evaluation means for evaluating a health condition based on information data related to the user's exercise information, the user's nutritional information, or the user's biological information transmitted from the client terminal or the wearable terminal.

By providing the evaluation means, it becomes easy for specialists on exercise and nutrition and doctors to give appropriate advice to users.

It is preferable that the health management system of the present invention is provided with a communication means capable of transmitting and receiving data by text message, voice call or video call between two or more of a client terminal, a service providing server and a doctor server.

In general, users who continue exercising and dieting often have anxiety and doubts. By providing the communication means, the user can ask questions to specialists and confide their worries in real time. Further, when a video call is possible as the communication means, it is also possible to conduct the interview between the users and specialists by using the communication means.

In the health management system of the present invention, the communication means may be a closed communication means operated except for the client terminal and the wearable terminal used by the user. Further, the closed communication means and the communication means in which the terminal used by the user is not excluded may be used in combination or switched.

In general, maintaining motivation is a major issue for the user who continues to exercise and diet. When the user's motivation is low, it may be necessary to make the user's mind positive and encouraged. Therefore, by using the closed communication means, for example, it becomes possible to talk only between specialists about contents that are difficult to convey to the user and improve the motivation of the user.

The health management system of the present invention may further include a user's family doctor terminal used by the user's family doctor and capable of transmitting and receiving data connected to the network, and the user's family doctor terminal may be able to share the guidance instruction data checked by the doctor on exercise prescriptions and nutritional prescriptions.

Since the family doctor is a medical worker who is familiar to the user, by enabling the family doctor to share information in the health management system, the system can be used more safely and securely by the user.

A device of the present invention is a device for assisting exercise prescription and nutrition prescription by a doctor. The guidance instruction issuance assisting device includes an identification information registration means for inputting user identification information data, a medical interview information registration means for inputting medical interview information data including lifestyle-related interviews, a guidance instruction issuance request means for inputting the guidance instruction issuance request data regarding exercise prescription and nutrition prescription by the doctor based on the identification information data and the medical interview information data, a guidance instruction automatic creation means for automatically creating guidance instruction data on exercise prescriptions and nutritional prescriptions, including exercise content and daily activity, based on information data acquired from the guidance instruction issuance request means, a guidance instruction manual correction means for correcting the automatically created guidance instruction data with referring to the medical interview information data by the operation of the doctor who has specialized knowledge about lifestyle-related diseases, metabolic syndrome, and locomotive syndrome, and a guidance instruction issuance means for outputting the guidance instruction that has been checked by the doctor who has specialized knowledge about exercise prescriptions and nutrition prescriptions based on medical interview information data.

It is preferable that the guidance instruction issuance assisting device of the present invention further includes an interview information registration means for inputting interview information data based on an interview result between an exercise or nutrition specialist and a user, and the guidance instruction manual correction means uses the interview information data for correction.

It is preferable that the guidance instruction issuance assisting device of the present invention further includes a means for selecting a health improvement course suitable for the user, and the guidance instruction automatic creation means automatically creates guidance instruction data based on the identification information data, the medical interview information data and the selected health improvement course.

A guidance instruction issuance assisting method of the present invention is a method of assisting an exercise prescription and nutritional prescription by a doctor, and includes the following steps 1) to 6).

1) Identification information registration step for inputting user identification information data.
2) Medical interview information registration step for inputting medical interview information data.

3) Guidance instruction issuance request step for requesting data of guidance instruction regarding exercise prescriptions and nutritional prescriptions by a doctor based on identification information data and medical interview information data.
4) Guidance instruction automatic creation step for automatically creating guidance instruction data based on the information data acquired from the guidance instruction issuance request step.
5) Guidance instruction manual correction step for correcting the automatically created guidance instruction data by a doctor.
6) Guidance instruction issuance step for outputting the guidance instruction data that has been checked by a doctor.

It is preferable that the guidance instruction issuance assisting method of the present invention further includes 7) Interview information registration step for inputting interview information data based on the interview result between an exercise or nutrition specialist and a user, and 5) Guidance instruction manual correction step which uses the interview information data for correction.

It is preferable that the guidance instruction issuance assisting method of the present invention further includes a step of selecting a health improvement course suitable for the user, and the guidance instruction automatic creation step automatically creates guidance instruction data based on the identification information data, the medical interview information data and the selected health improvement course.

According to the health management system of the present invention, there is an effect that specialists in exercise and nutrition can cooperate to safely and continuously support the health of each patient. Further, according to the guidance instruction issuance assisting device and method of the present invention, there is an effect that the doctor can safely and smoothly prescribe exercise and nutrition.

MODES FOR CARRYING OUT THE INVENTION

Embodiments of the present invention will be described in detail below with reference to the drawings. The present invention is not limited to the following embodiments and examples shown in the figures, and the present invention can be variously changed in design.

Embodiment 1

Figure 1:
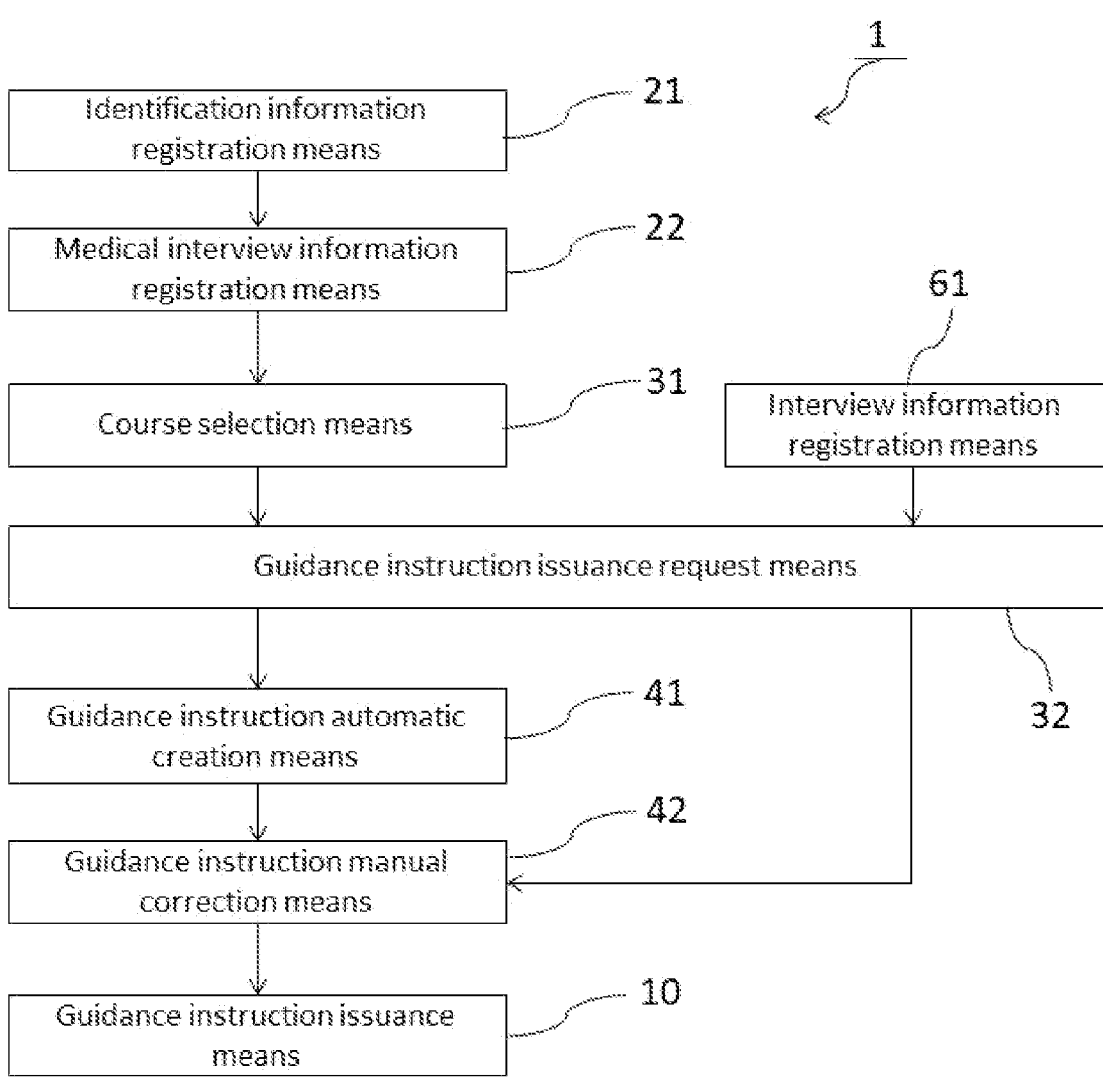
FIG. 1 Functional block diagram of the guidance instruction issuance assisting device according to a first embodiment.
Figure 2:
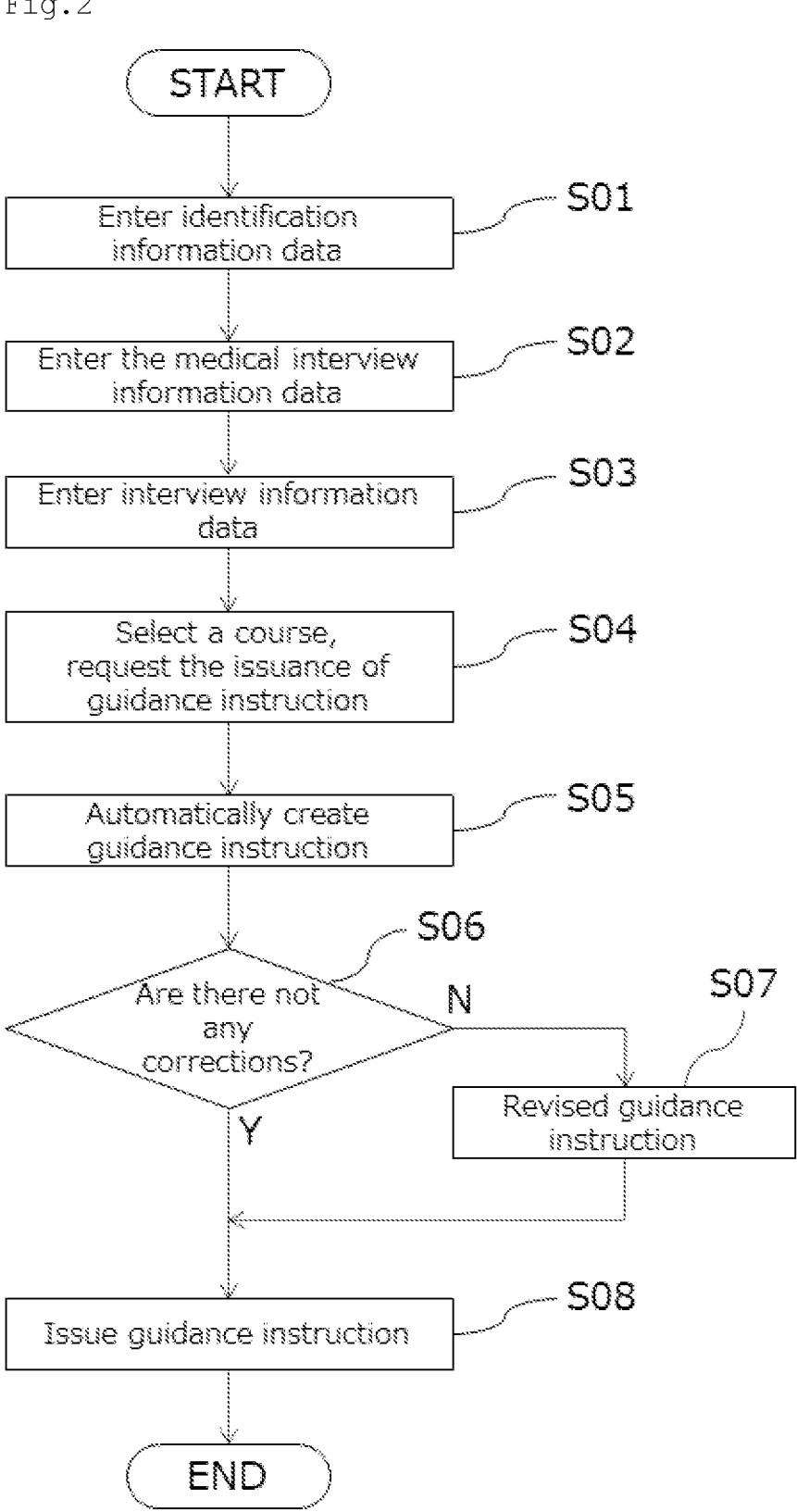
FIG. 2 Schematic flow diagram of the guidance instruction issuance assisting method of the first embodiment.

FIG. 1 shows a functional block diagram of the guidance instruction issuance assisting device of the first embodiment. Further, FIG. 2 shows a schematic flow chart of the guidance instruction issuance assistance method of the first embodiment. As shown in FIG. 1, the guidance instruction issuance assisting device 1 includes the identification information registration means 21, the medical interview information registration means 22, the course selection means 31, the guidance instruction issuance request means 32, the guidance instruction automatic creation means 41, the guidance instruction manual correction means 42, the guidance instruction issuance means 10 and the interview information registration means 61.

As shown in FIG. 2, first, the user inputs the identification information data (step S01). The identification information registration means 21 shown in FIG. 1 registers the identification information data of the user, and the identification information data may include a name, an e-mail address, and the like, and the gender, date of birth, weight, height, and body fat mass and the like.

Next, the medical interview information data is input (step S02). The medical interview information registration means 22 shown in FIG. 1 registers the contents of the user's response to the medical interview, and the medical interview information data includes not only the medical interview related to the lifestyle but also the information related to the medical examination result. Examples of medical interviews include questions about medicines and the like such as "Are you taking medications that lower blood pressure?", "Are you taking insulin injections or medications that lower blood sugar?" or "Are you taking medications that lower cholesterol?" and questions about chronic diseases such as "Have you ever been told or treated by a doctor for heart disease?". In addition to heart disease, the diseases to be questioned include, for example, stroke (cerebral hemorrhage, cerebral infarction, etc.) and chronic renal failure.

After the identification information data and the medical interview information data are input, the first interview is conducted between the exercise or nutrition specialist and the user. An exercise specialist is, for example, a health exercise instructor, and a nutrition specialist is, for example, a registered dietitian. It is preferable that the interview between the user and the above specialist is performed by a video call using the Internet, but this is not limited to this, and the interview may be conducted by actually meeting, or voice call as simple methods. Based on the interview, the specialist inputs the interview information data (step S03). The interview information registration means 61 shown in FIG. 1 registers the information obtained in the interview conducted between the user and the specialist on exercise or nutrition.

Next, a course is selected and a guidance instruction issuance is requested (step S04). The course selection means 31 selects a health improvement course suitable for the user, and it is conceivable that, for example, a course such as a "lifestyle-related disease improvement course" or a "sarcopenia course" can be selected. The course selection is preferably made by the exercise or nutrition specialist, but may be configured to be user selectable, for example. The health improvement course is not limited to the above-mentioned "lifestyle-related disease improvement course" and "sarcopenia course".

The guidance instruction issuance request means 32 shown in FIG. 1 requests the issuance of the guidance instruction by the specialist doctor based on the identification information data, the medical interview information data, the health improvement course, and the interview information data.

Upon receiving a request to issue the guidance instruction, the guidance instruction is automatically created (step S05). The guidance instruction automatic creation means 41 shown in FIG. 1 automatically creates the guidance instruction data based on the information acquired from the guidance instruction issuance request means 32.

If there is a part of the automatically created guidance instruction data that needs to be corrected (step S06), the guidance instruction is corrected (step S07). The guidance instruction manual correction means 42 shown in FIG. 1 can manually correct the guidance instruction data automatically created, and the correction is performed by the specialist doctor. When the guidance instruction manual correction means 42 manually corrects the guidance instruction data, the guidance instruction manual correction means 42 can make the correction while referring to the interview information data registered by the interview information registration means 61.

If there is no part of the automatically created guidance instruction data that needs to be corrected (step S06), the guidance instruction is issued (step S08). The guidance instruction issuance means 10 shown in FIG. 1 issues the guidance instruction, and the automatically created guidance instruction data is issued as the guidance instruction after being checked by the specialist doctor.

Figure 3:
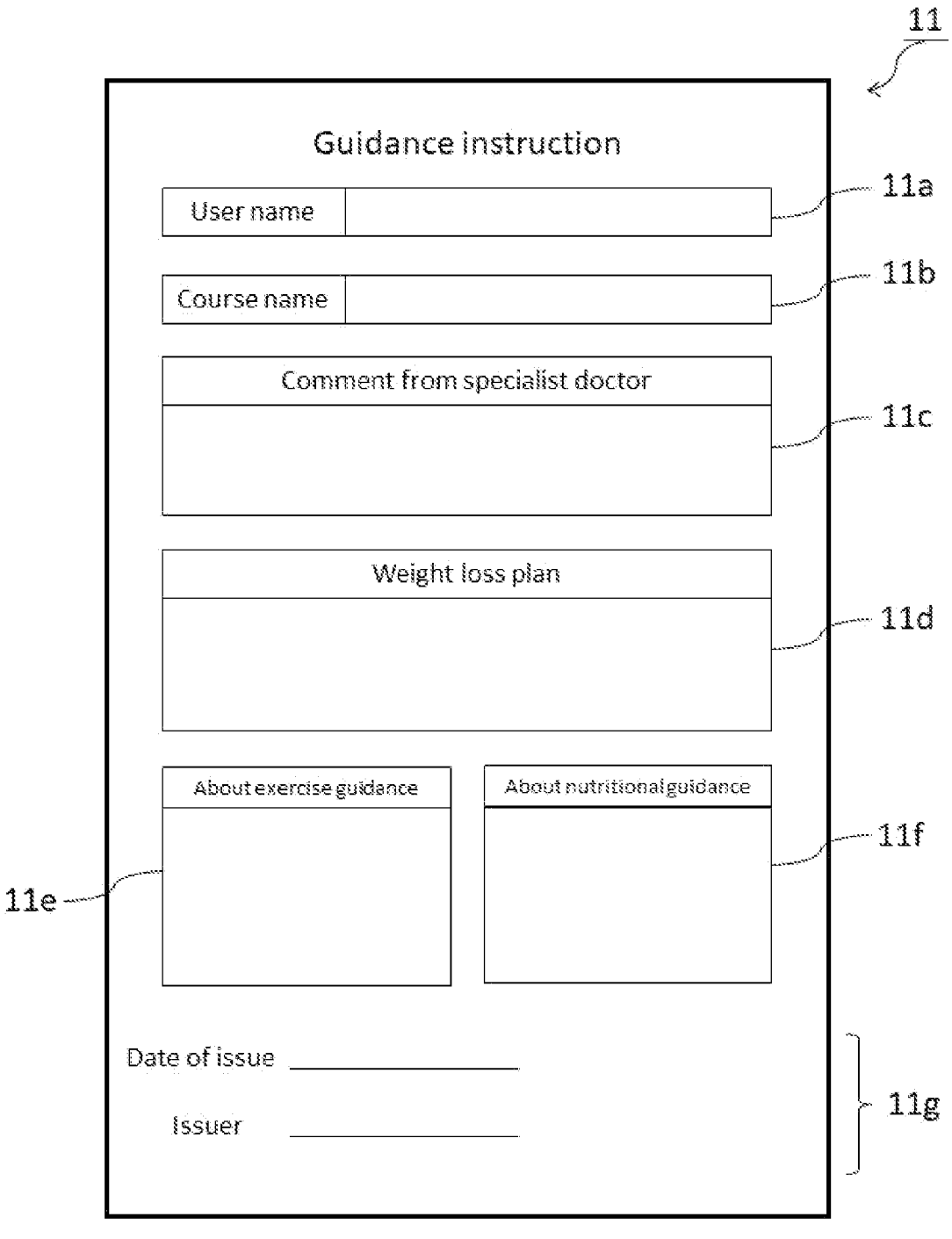
FIG. 3 Image diagram of the guidance instruction.

FIG. 3 is an image diagram of the guidance instruction and shows an example of the guidance instruction. As shown in FIG. 3, the guidance instruction 11 includes a user name display column 11*a*, a course name display column 11*b*, a specialist doctor comment display column 11*c*, a weight loss plan display column 11*d*, an exercise prescription display column 11*e*, a nutrition prescription display column 11*f* and an issuer display column 11*g*.

A user name is displayed in the user name display column 11*a*.

In the course name display column 11*b*, the health improvement course selected by the course selection means 31 is basically displayed in the state where the guidance instruction data is automatically created. For example, if the health exercise instructor who interviewed the user determines that the "lifestyle-related disease improvement course" is suitable for the user and is selected, "lifestyle-related disease improvement course" is displayed in the course name display column 11*b* of the guidance instruction data. If the specialist doctor determines that the "sarcopenia course" is more suitable for the user, it can be modified to the "sarcopenia course".

In the specialist doctor comment display column 11*c*, a text comment from the specialist doctor is displayed. In the specialist doctor comment display column 11*c*, in the state where the guidance instruction data is automatically created, comments are displayed by automatic creation for the items for which a negative answer is given in the medical interview about lifestyle habits. Here, the comments are displayed in order from the one with the highest importance. The specialist doctor can add/correct the automatically created comment in free text while referring to the user's identification information, medical interview information and interview information data. As a comment, for example, regarding nutrition, an example such as "listing recommended or not recommended foods" can be considered.

In the weight loss plan display column 11d, "current weight", "target weight", "period", "weight loss pace" and the like are displayed. Here, regarding the weight loss pace, the weight loss pace per month is displayed by body weight or percentage, for example, "2 kg per month" or "4% per month". Depending on the health of the user, weight loss may not be necessary. In such a case, the "current weight" and the "target weight" are the same, and the weight loss pace is also displayed as "0 kg per month".

In the exercise prescription display column 11e, for example, "resistance exercise" and "daily activity amount" are displayed. The resistance exercise is an exercise that repeatedly applies resistance to the muscles, and the displayed contents are "frequency of exercise" such as how many times a week exercise is done, and "execution time per exercise" and "expected calories burned" are displayed. As the amount of activity per day, "target number of steps" and "calories burned" are displayed.

In the nutrition prescription display column 11f, the content related to "dietary restriction" is displayed. Specifically, "calorie intake per day" and "calorie intake per meal" are displayed. Here, the "calorie intake per meal" is displayed as a numerical value obtained by dividing the "calorie intake per day" by 3, and is used as a guideline.

In the issuer display column 11g, the issue date of the guidance instruction and the name and affiliation of the specialist doctor who checked the automatically created guidance instruction data are displayed.

In addition, for example, even if it is a lifestyle-related disease, there are cases where it is not necessary to lose weight because it is a lipid abnormality, hypertension, or the like. Therefore, even if the course name displayed in the course name display column 11b is "lifestyle-related disease improvement course", at the discretion of the specialist doctor, it is also possible to describe not the content related to the prevention and improvement of metabolic syndrome but the content related to the prevention and improvement of locomotive syndrome in the exercise prescription display column 11e and the nutrition prescription display column 11f.

Further, the guidance instruction 11 may be issued as an electronic file, or for example, the guidance instruction 11 printed out may be sent to the user or the like.

Embodiment 2

Figure 4:
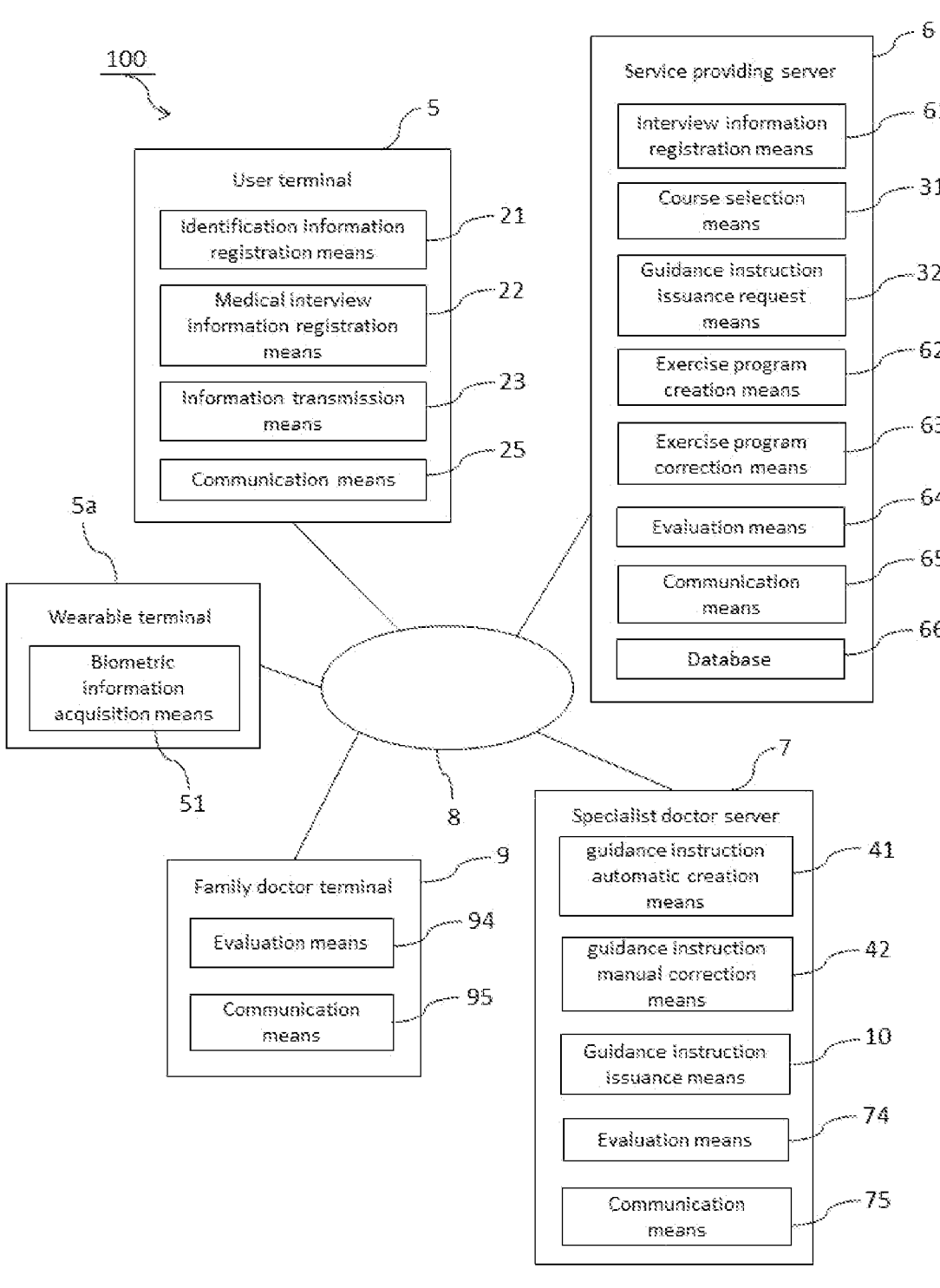
FIG. 4 System configuration diagram of the health management system of a second embodiment.

In a second embodiment, the health management system will be described. FIG. 4 shows a system configuration diagram of the health management system of the second embodiment. As shown in FIG. 4, in the health management system 100, the user terminal 5, the wearable terminal 5a, the service providing server 6, the specialist doctor server 7, and the family doctor terminal 9 can share information data via the Internet 8.

The user terminal 5 is provided with an identification information registration means 21, a medical interview information registration means 22, an information transmission means 23 and a communication means 25. The wearable terminal 5a is provided with a biometric information acquisition means 51. The service providing server 6 is provided with an interview information registration means 61, a course selection means 31, a guidance instruction issuance request means 32, an exercise program creation means 62, an exercise program correction means 63, an evaluation means 64, a communication means 65 and a database 66. The specialist doctor server 7 is provided with a guidance instruction automatic creation means 41, a guidance instruction manual correction means 42, a guidance instruction issuance means 10, an evaluation means 74 and a communication means 75. The family doctor terminal 9 is provided with an evaluation means 94 and a communication means 95.

(Issuance of Guidance Instruction)

Figure 5:
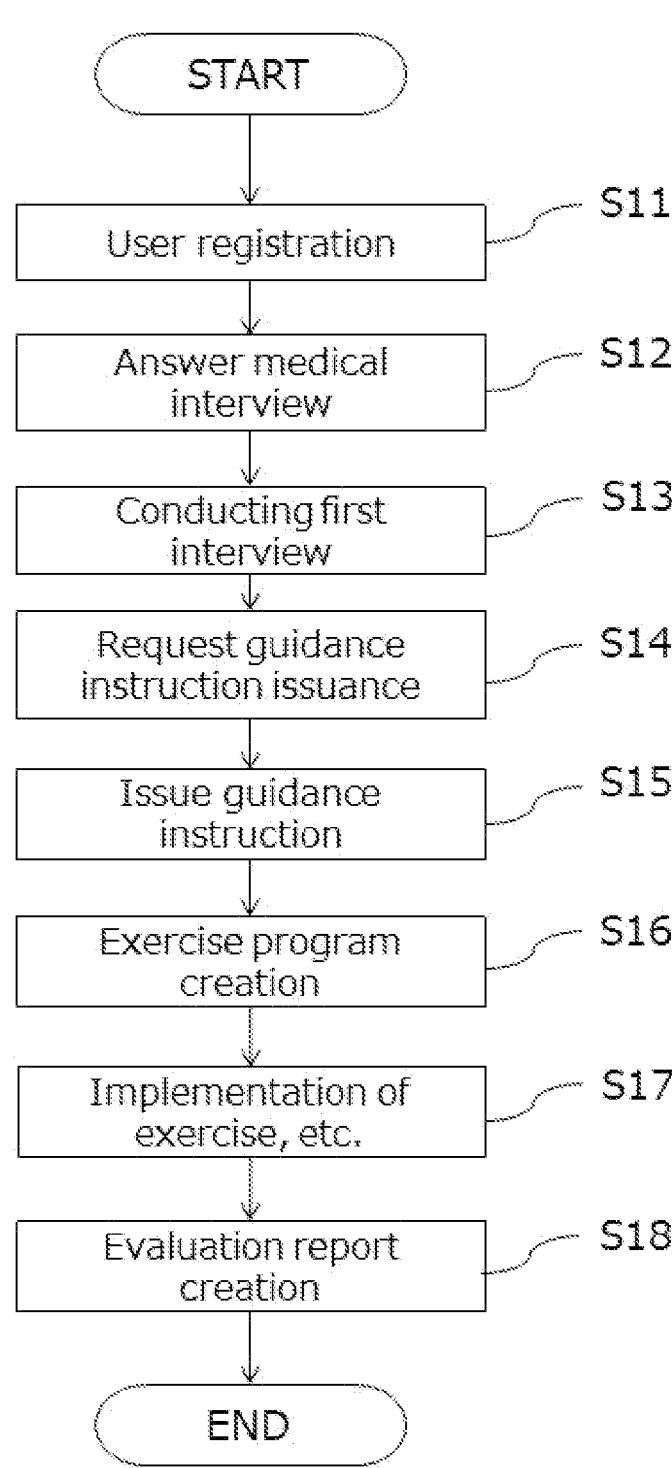
FIG. 5 Schematic flow chart of the health management service of the second embodiment.

FIG. 5 shows a schematic flow chart of a health management service. Further, FIG. 6 shows a flow chart for issuing a guidance instruction for the health management system of the second embodiment.

As shown in FIG. 5, in the health management service, a user (not shown) registers as a user (step S11). Registration is performed using the user terminal 5 such as a smartphone, a PC, or a tablet terminal owned by the user. Specifically, as shown in FIG. 6, the identification information data is input (step S101) using the identification information registration means 21 provided in the user terminal 5 shown in FIG. 4, and the identification information data is transmitted to the service providing server 6 (step S102). The service providing server 6 receives the identification information data (step S103) and stores it in a database 66.

Figure 6:
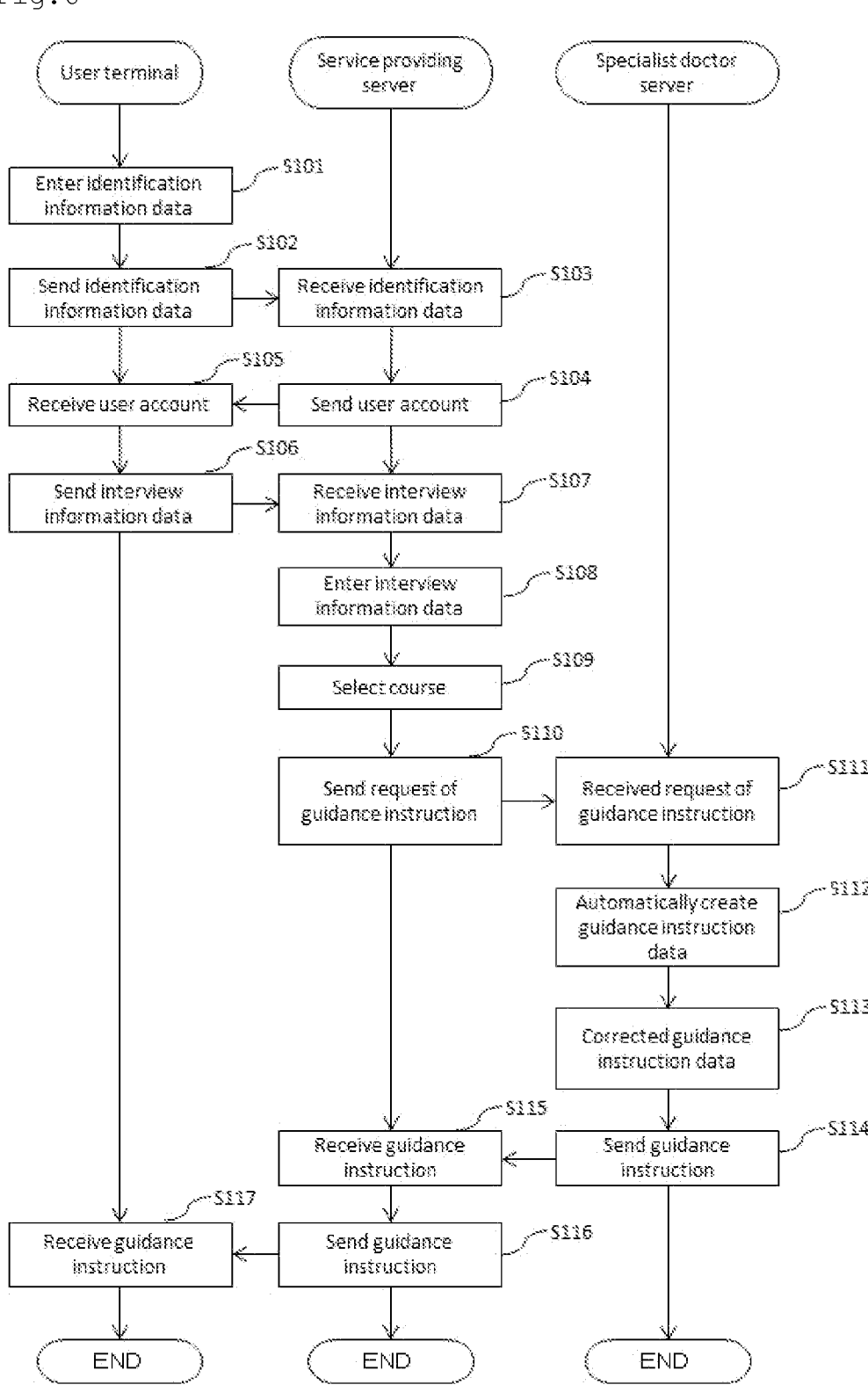
FIG. 6 Flow diagram of the guidance instruction issuance of the health management system of the second embodiment.

The service providing server 6, after the registration of the identification information data, issues a user account, and transmits data related to the user account to the user terminal 5 as shown in FIG. 6 (step S104). The user terminal 5 receives data related to the user account (step S105).

The user may use the health management service, for example, by referral from the family doctor, but the family doctor does not register, but the user himself performs the registration procedure.

As shown in FIG. 5, after the user registration, the user answers the medical interview (step S12). The user uses the medical interview information registration means 22 provided in the user terminal 5 shown in FIG. 4 to transmit the medical interview information data to the service providing server 6 as shown in FIG. 6 (step S106). The service providing server 6 receives the medical interview information data (step S107) and stores it in the database 66.

After the identification information data and the medical interview information data are registered, the first interview is performed between the exercise or nutrition specialist and the user as shown in FIG. 5 (step S13). In this embodiment, the exercise specialist is a health exercise instructor (not shown), and the nutrition specialist is a registered dietitian (not shown). The health exercise instructor and the registered dietitian are staff members who belong to a service provider (not shown).

The communication means (25, 65, 75, 95) shown in FIG. 4 can send and receive data by text message, voice call, or video call between two or more parties. The interview between the specialist and the user is performed here by a video call using the Internet using a communication means (25, 65), but the interview may instead be performed by a communication means other than the communication means (25, 65). Alternatively, the above-mentioned expert and the user may actually meet and have an interview. The interview is conducted by the user and at least one of a health exercise instructor or a registered dietitian, but the health exercise instructor and the registered dietitian may participate together. In addition, a plurality of health exercise instructors and registered dietitians may participate.

As shown in FIG. 6, the specialist registers the interview information data obtained as the result of such the interview in the service providing server 6 using the interview information registration means 61 shown in FIG. 4 (Step S108), and it is stored in the database 66.

After the initial interview is carried out, as shown in FIG. 5, the health exercise instructor or the registered dietitian requests a specialist doctor (not shown) to issue the guidance instruction (step S14). Specifically, the course selection means 31 shown in FIG. 4 is used to select a course as shown in FIG. 6 (step S109). After selecting the course, the health exercise instructor or the registered dietitian sends a guidance instruction issuance request from the service providing server 6 to the specialist doctor server 7 by using the guidance instruction issuance request means 32 (step S110). The specialist doctor server 7 receives the guidance instruction issuance request (step S111).

As shown in FIG. 5, the specialist doctor issues the guidance instruction in response to the request from the health exercise instructor or the registered dietitian to issue the guidance instruction (step S15). Specifically, the guidance instruction automatic creation means 41 provided in the specialist doctor server 7 shown in FIG. 4 automatically creates the guidance instruction data (step S112). The specialist doctor uses the guidance instruction manual correction means 42 provided on the specialist server 7 to make necessary corrections to the guidance instruction data (step S113). The data related to the guidance instruction that has been checked by the specialist doctor is transmitted from the specialist doctor server 7 to the service providing server 6 (step S114). The service providing server 6 receives the data related to the guidance instruction (step S115) and stores it in the database 66. The service providing server 6 transmits data related to the guidance instruction to the user terminal 5 (step S116). The user terminal receives the data related to the guidance instruction (step S117).

Here, an example is shown in which the data related to the guidance instruction is transmitted from the specialist doctor server 7 in the order of the service providing server 6 and the user terminal 5. For example, it may be transmitted to the service providing server 6 at the same time, or it may be transmitted only to the service providing server 6, and the user, the specialist doctor or the family doctor may be able to view the guidance instruction by accessing the data. In this way, since the guidance instruction is issued as an electronic file, the entire process from user registration to issuance of the guidance instruction can be performed on the web, which is a highly convenient service.

(About Creating an Exercise Program)

As shown in FIG. 5, after issuing the guidance instruction, the exercise program is created based on the guidance instruction (step S16). The service providing server 6 automatically creates the exercise program by using the exercise program creating means 62 based on the received data on the guidance instruction. In addition, the health exercise instructor can modify the content of the automatically created exercise program by using the exercise program modifying means 63.

In this embodiment, the exercise program is created based on the content of the guidance instruction, but unlike this, for example, before the guidance instruction is issued, the exercise program is automatically created based on the identification information, the medical interview information data and the selected health improvement course by using the exercise program creation means 62, and after issuing the guidance instruction, the content of the automatically created exercise program can be modified by using the exercise program modifying means 63. By tentatively creating the exercise program before issuing the guidance instruction, the exercise program can be quickly provided to the user.

Figure 7:
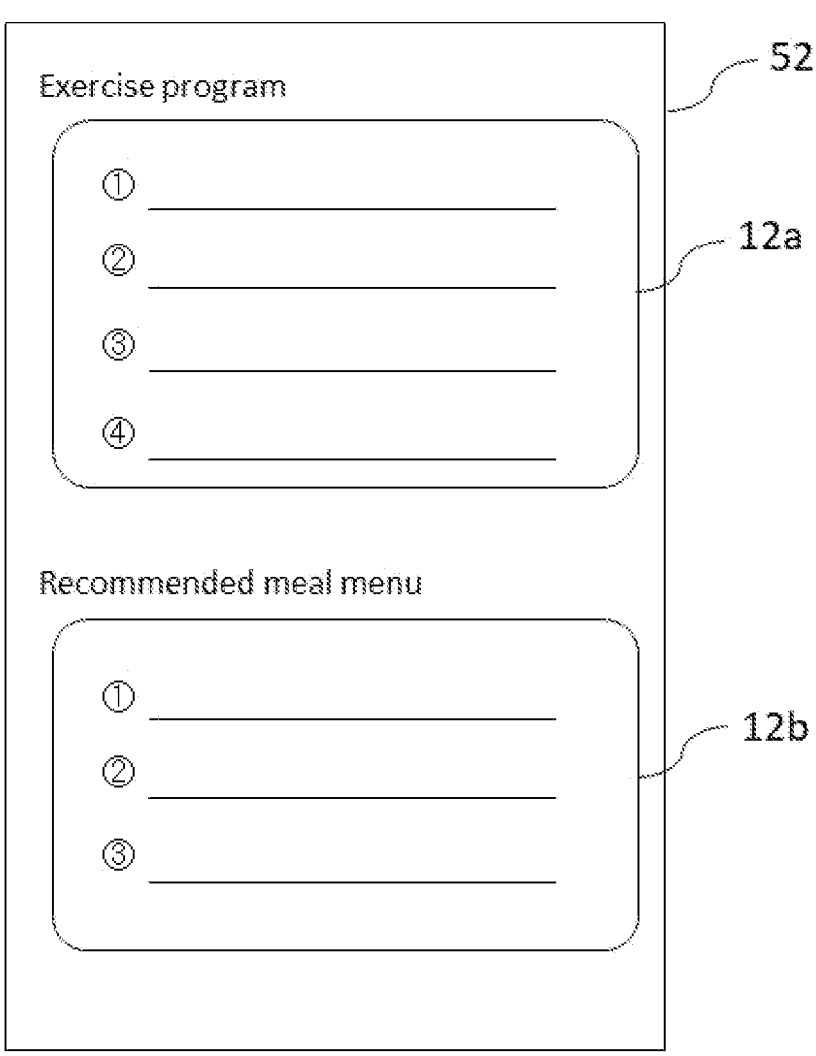
FIG. 7 Screen image of the exercise program and meal menu.

The exercise program automatically created and checked by the health exercise instructor is transmitted to the user terminal 5. FIG. 7 shows a screen image diagram of the exercise program and the meal menu. As shown in FIG. 7, the exercise program display column 12a and the recommended meal menu display column 12b are displayed on the screen 52 of the user terminal 5. The above-mentioned exercise program is displayed in the exercise program display column 12a. In addition, the registered dietitian can create a recommended meal menu based on the calorie intake described in the guidance instruction and the recommended meal menu is displayed in the recommended meal menu display column 12b.

(About an Implementation of Exercise, Etc.)

The user carries out training according to the created exercise program. In addition, the user controls the daily calorie intake based on the dietary restriction content described in the guidance instruction.

Regarding the training implementation result and daily calorie intake, the user uses the user terminal 5 to transmit data to the service providing server 6 via the Internet 8, and the service providing server 6 stores the received data in the database 66.

Further, the wearable terminal 5a is provided with the biological information acquisition means 51. The biometric information data here is a pulse rate, a heart rate, a respiratory rate, a body temperature, a step count, a moving distance, a floor number, a calorie consumption, etc., and the wearable terminal 5a obtains the biometric information data from the biometric information acquisition means 51. The biometric information data is transmitted to the service providing server 6 through the Internet 8, and the service providing server 6 stores the received biometric information data in the database 66.

The training results, biometric information data, etc. stored in the database 66 can be viewed on the service providing server 6. It can also be viewed on the user terminal 5, the specialist doctor server 7, and the family doctor terminal 9 through the Internet 8.

Users often have anxiety and doubts as they continue to exercise and diet. As shown in FIG. 4, the user terminal 5, the service providing server 6, the specialist doctor server 7, and the family doctor terminal 9 are provided with the communication means (25, 65, 75, 95). As a result, the user who uses the user terminal 5, the health exercise instructor who uses the service providing server 6, the management staff such as the registered dietitian, the specialist doctor who uses the specialist doctor server 7, and the family doctor (not shown) who uses the family doctor terminal 9 can communicate with each other using the communication means (25, 65, 75, 95). As described above, the communication means (25, 65, 75, 95) can send and receive data by text message, voice call, or video call between two or more parties.

Figure 8:
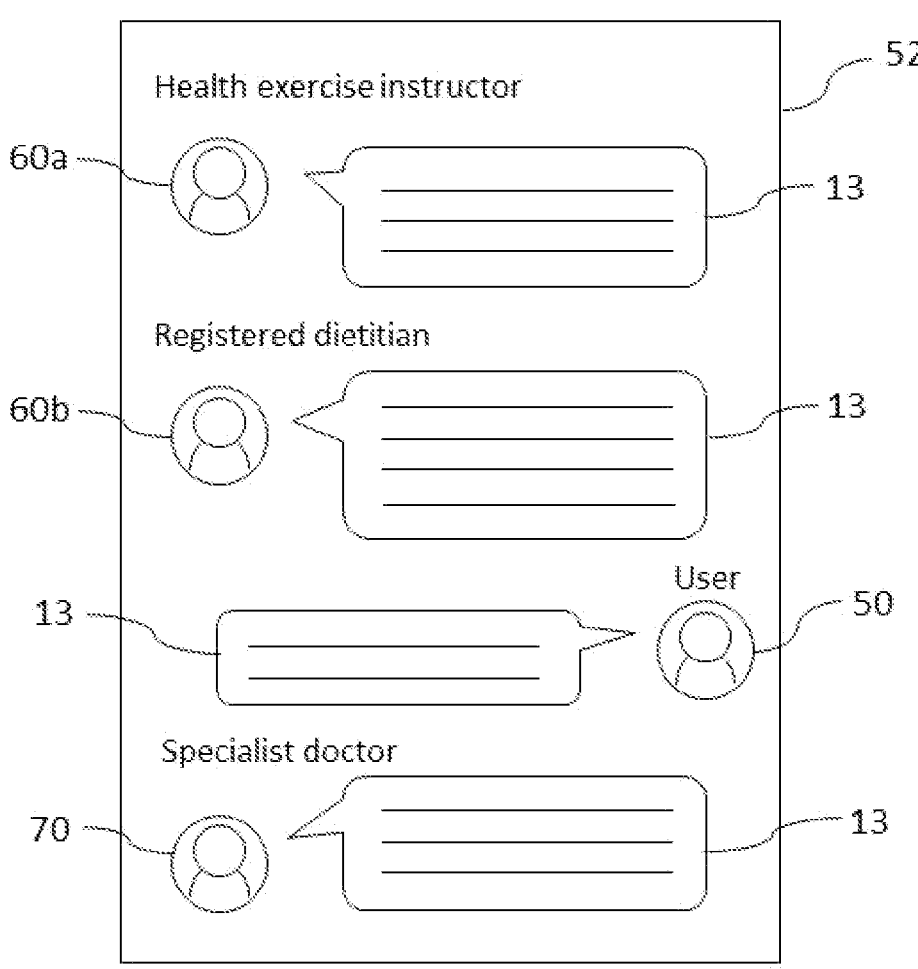
FIG. 8 Chat screen image of the second embodiment.

FIG. 8 shows the chat screen image of the second embodiment. As shown in FIG. 8, on the screen 52 of the user terminal 5, the icons of the health exercise instructor 60a, the registered dietitian 60b, the user 50, and the specialist doctor 70, and the text message 13 by each are displayed. In this way, a group in which the health exercise instructor 60a, the registered dietitian 60b, the user 50, and the specialist doctor 70 participate is generated, and the conversation by text or the like becomes possible, so that the user can easily ask the specialist questions, and anxiety and doubts can be easily resolved while continuing exercises and dietary restrictions. Although not shown here, the family doctor can also participate in the group chat as shown in FIG. 8.

By communication using the communication means (25, 65, 75, for example, the health exercise instructor 60a can change the exercise program within the range of the guidance instruction according to the wishes of the user 50. In addition, the registered dietitian 60b can modify the nutritional guidance contents such as the recommended meal menu within the scope of the guidance instruction in accordance with the change of the exercise program. Further, for example, when the health exercise instructor 60a or the registered dietitian 60b determines that the health condition of the user 50 is significantly improved and it is better to have the guidance instruction reissued, the guidance instruction is given. A reissue request can be proposed to the user 50, and after obtaining the consent of the user 50, the specialist doctor can be requested to reissue the guidance instruction. The instruction reissue request is made by the guidance instruction issuance request means 32 provided in the service providing server 6, but the communication means (65, 75) may also be used.

(About an Evaluation Report)

As shown in FIG. 5, after the user exercises or restricts the diet for a certain period of time, the health exercise instructor or the registered dietitian creates the evaluation report using the evaluation means 64 based on the training results and biometric information data stored in the database 66 (step S18).

Figure 9:
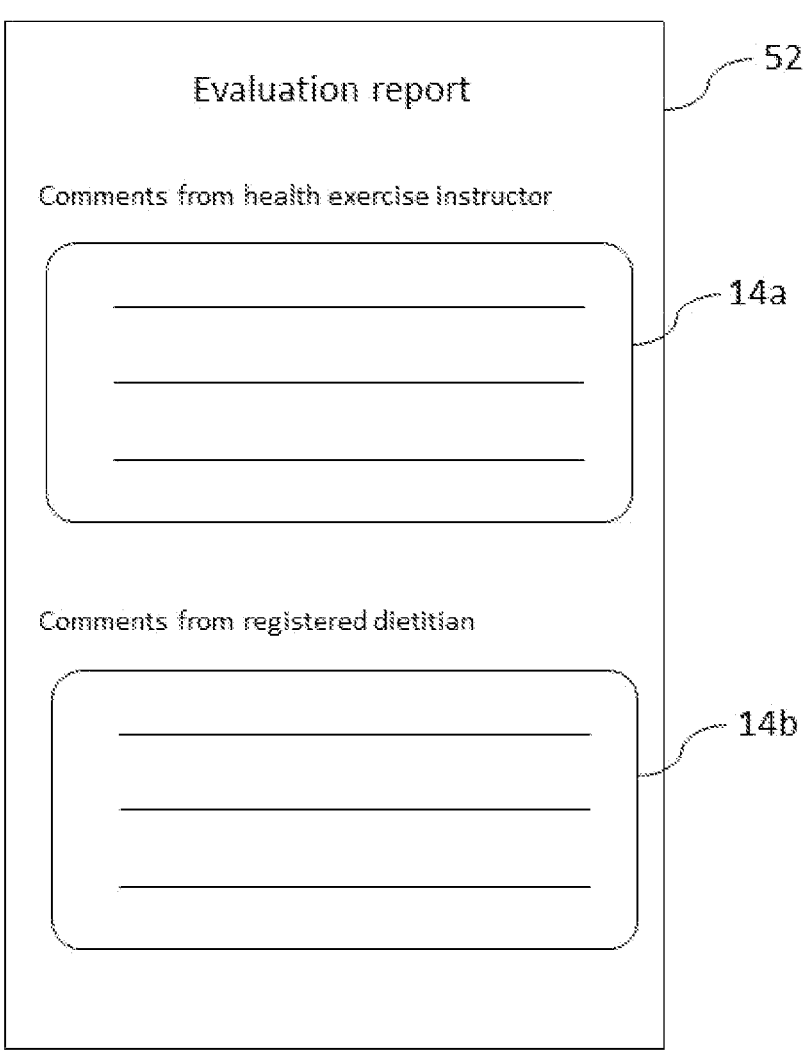
FIG. 9 Evaluation report screen image.

FIG. 9 shows the evaluation report screen image. As shown in FIG. 9, the comment 14a from the health exercise instructor and the comment 14b from the registered dietitian are displayed as text on the screen 52 of the user terminal 5. In the evaluation report, for example, a comment urging the reissue of the guidance instruction may be added. Further, the evaluation report can be created by the specialist doctor using the evaluation means 74 or by the family doctor using the evaluation means 94.

In this embodiment, the evaluation report is created once every two weeks, but it is possible to adjust the issuance frequency such as once a month or once a week according to the needs of the user.

SUMMARY

According to the health management system of the second embodiment, a plurality of health experts can work together as one team to improve the health condition while being close to each user. Since the user can carry out an exercise program or the like under the guidance of specialists, it is possible to carry out safe, secure and effective training and dietary improvement.

In addition, since the entire process from user registration to evaluation report can be performed on the web, it can be easily used anywhere and at any time, and it can be said that it is a highly convenient system.

Embodiment 3

In the health management system of the third embodiment, the communication means 25 provided in the user terminal 5 shown in FIG. 4 can limit the function of communicating by text message.

Figure 10:
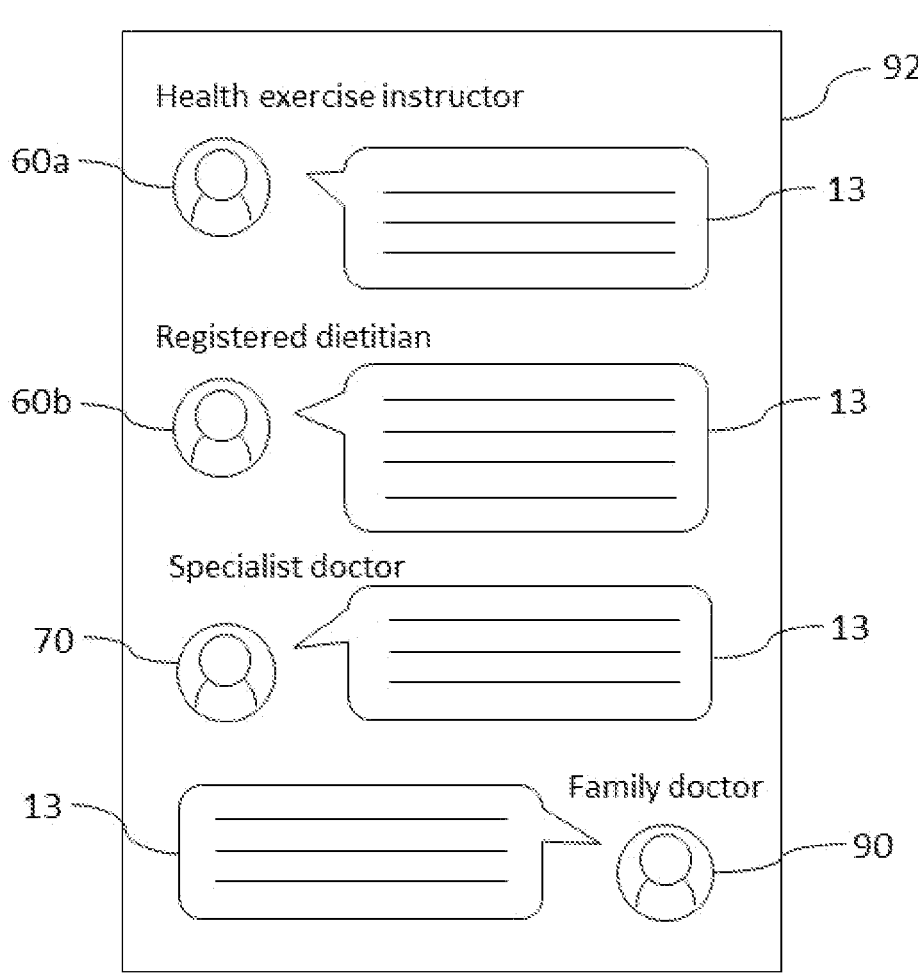
FIG. 10 Chat screen image of a third embodiment.

FIG. 10 shows an image diagram of the chat screen of the third embodiment. As shown in FIG. 10, on the screen 92 of the family doctor terminal 9 used by the family doctor 90, the icons of the health exercise instructor 60a, the registered dietitian the specialist 70, and the family doctor 90, and text messages 13 by each of them is displayed. However, unlike FIG. 8, the user 50 and the comment 13 by the user 50 are not displayed.

In general, maintaining motivation is a major challenge for users who continue to exercise and diet. When the user's motivation is low, it may be necessary to make the user's mind positive and encouraged. Therefore, a group in which the health exercise instructor 60a, the registered dietitian 60b, the specialist 70, and the family doctor 90 participate is generated, and conversations can be made by texts or the like. It is possible to have a conversation only between specialists.

Also, by switching to or using a chat group in which the user can participate, it is possible to deliver an appropriate message to the users as needed, and it is possible to increase the motivation for improving the health condition of the users.

Other Embodiments

1) In FIG. 4, the identification information registration means 21, the medical interview information registration means 22 and the communication means 25 are provided in the user terminal 5. Any of the applications may be installed and used in the user terminal 5, or may be provided in the service providing server 6 and the specialist may access and use the service providing server 6 through the Internet 8 or the like.

2) In FIG. 4, the guidance instruction automatic creation means 41, the guidance instruction manual correction means 42, the guidance instruction issuance means 10, the evaluation means 74 and the communication means 75 are provided in the specialist server 7. Any of the applications may be installed and used in the specialist server 7, or may be provided in the service providing server 6 and the specialist may access and use the service providing server 6 through the Internet 8 or the like.

3) In FIG. 4, the evaluation means 94 and the communication means 95 are provided in family doctor terminal 9. Any of the applications may be installed and used in the family doctor terminal 9, or may be provided in the service providing server 6 and the family doctor may access and use the service providing server 6 through the Internet 8 or the like.

4) Unlike the second embodiment, the family doctor terminal 9 may not be used and the family doctor may not be involved.

5) The service providing server 6 may be configured to be further provided with means for aggregating vital data such as pulse rate on a daily basis and to be referred to when creating an evaluation report or the like.

6) The service providing server 6 may be provided with means for displaying the data stored in the database 66 in a graph.

[More about Operating Environments]

Figure 11:
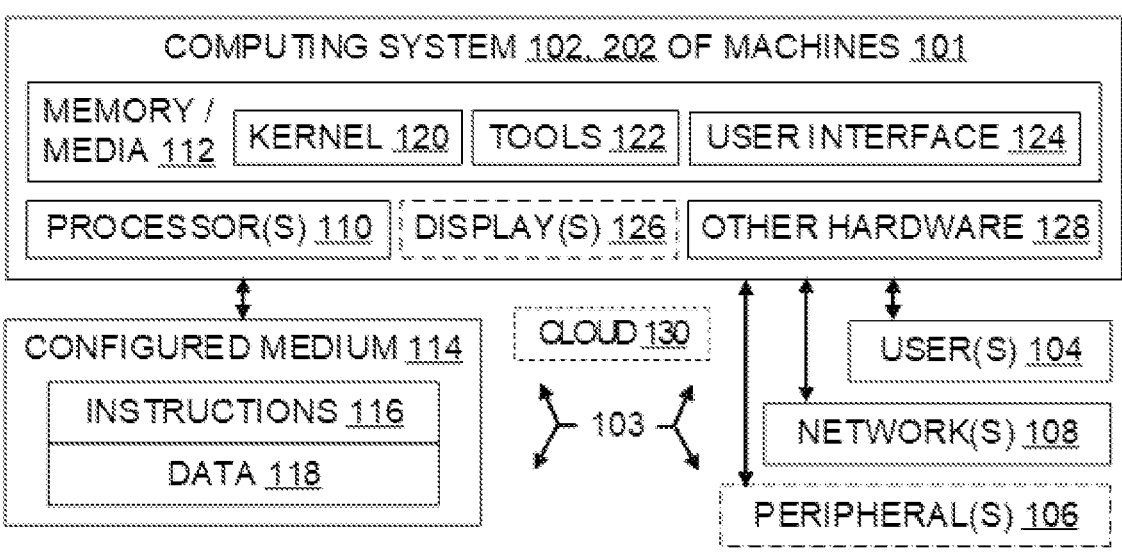
FIG. 11 Diagram illustrating aspects of computer systems and also illustrating configured storage media.

With reference to FIG. 11, an operating environment 103 for an embodiment includes at least one computer system 102. The computer system 102 may be a multiprocessor computer system, or not. An operating environment may include one or more machines in a given computer system, which may be clustered, client-server networked, and/or peer-to-peer networked within a cloud 130. An individual machine is a computer system, and a network or other group of cooperating machines is also a computer system. A given computer system 102 may be configured for end-users, e.g., with applications, for administrators, as a server, as a distributed processing node, and/or in other ways.

Human users 104 may interact with a computer system 102 user interface 124 by using displays 126, keyboards 106, and other peripherals 106, via typed text, touch, voice, movement, computer vision, gestures, and/or other forms of I/O. Virtual reality or augmented reality or both functionalities may be provided by a system 102. A screen 126 may be a removable peripheral 106 or may be an integral part of the system 102. The user interface 124 may support interaction between an embodiment and one or more human users. The user interface 124 may include a command line interface, a graphical user interface (GUI), natural user interface (NUI), voice command interface, and/or other user interface (UI) presentations, which may be presented as distinct options or may be integrated.

System administrators, network administrators, cloud administrators, security analysts and other security personnel, operations personnel, developers, testers, engineers, auditors, and end-users are each a particular type of human user 104. Automated agents, scripts, playback software, devices, and the like running or otherwise serving on behalf of one or more humans may also have accounts, e.g., service accounts. Sometimes an account is created or otherwise provisioned as a human user account but in practice is used primarily or solely by one or more services; such an account is a de facto service account.

Storage devices and/or networking devices may be considered peripheral equipment in some embodiments and part of a system 102 in other embodiments, depending on their detachability from the processor 110. Other computer systems not shown in FIG. 11 may interact in technological ways with the computer system 102 or with another system embodiment using one or more connections to a cloud 130 and/or other network 108 via network interface equipment, for example.

Each computer system 102 includes at least one processor 110. The computer system 102, like other suitable systems, also includes one or more computer-readable storage media 112, also referred to as computer-readable storage devices 112. Tools 122 may include software apps on mobile devices 102 or workstations 102 or servers 102, as well as APIs, browsers, or webpages and the corresponding software for protocols such as HTTPS, for example.

Storage media 112 may be of different physical types. The storage media 112 may be volatile memory, nonvolatile memory, fixed in place media, removable media, magnetic media, optical media, solid-state media, and/or of other types of physical durable storage media (as opposed to merely a propagated signal or mere energy). In particular, a configured storage medium 114 such as a portable (i.e., external) hard drive, CD, DVD, memory stick, or other removable nonvolatile memory medium may become functionally a technological part of the computer system when inserted or otherwise installed, making its content accessible for interaction with and use by processor 110. The removable configured storage medium 114 is an example of a computer-readable storage medium 112. Some other examples of computer-readable storage media 112 include built-in RAM, ROM, hard disks, and other memory storage devices which are not readily removable by users 104. For compliance with current United States patent requirements, neither a computer-readable medium nor a computer-readable storage medium nor a computer-readable memory is a signal per se or mere energy under any claim pending or granted in the United States.

The storage device 114 is configured with binary instructions 116 that are executable by a processor 110; "executable" is used in a broad sense herein to include machine code, interpretable code, bytecode, and/or code that runs on a virtual machine, for example. The storage medium 114 is also configured with data 118 which is created, modified, referenced, and/or otherwise used for technical effect by execution of the instructions 116. The instructions 116 and the data 118 configure the memory or other storage medium 114 in which they reside; when that memory or other computer readable storage medium is a functional part of a given computer system, the instructions 116 and data 118 also configure that computer system. In some embodiments, a portion of the data 118 is representative of real-world items such as events manifested in the system 102 hardware, product characteristics, inventories, physical measurements, settings, images, readings, volumes, and so forth. Such data is also transformed by backup, restore, commits, aborts, reformatting, and/or other technical operations.

Although an embodiment may be described as being implemented as software instructions executed by one or more processors in a computing device (e.g., general purpose computer, server, or cluster), such description is not meant to exhaust all possible embodiments. One of skill will understand that the same or similar functionality can also often be implemented, in whole or in part, directly in hardware logic, to provide the same or similar technical effects. Alternatively, or in addition to software implementation, the technical functionality described herein can be performed, at least in part, by one or more hardware logic components. For example, and without excluding other implementations, an embodiment may include hardware logic components 110, 128 such as Field-Programmable Gate Arrays (FPGAs), Application-Specific Integrated Circuits (ASICs), Application-Specific Standard Products (ASSPs), System-on-a-Chip components (SOCs), Complex Programmable Logic Devices (CPLDs), and similar components. Components of an embodiment may be grouped into interacting functional modules based on their inputs, outputs, and/or their technical effects, for example.

In addition to processors 110 (e.g., CPUs, ALUs, FPUs, TPUs, GPUs, and/or quantum processors), memory/storage media 112, peripherals 106, and displays 126, an operating environment may also include other hardware 128, such as batteries, buses, power supplies, wired and wireless network interface cards, for instance. The nouns "screen" and "display" are used interchangeably herein. A display 126 may include one or more touch screens, screens responsive to input from a pen or tablet, or screens which operate solely for output. In some embodiments, peripherals 106 such as human user I/O devices (screen, keyboard, mouse, tablet, microphone, speaker, motion sensor, etc.) will be present in operable communication with one or more processors 110 and memory 112.

In some embodiments, the system includes multiple computers connected by a wired and/or wireless network 108. Networking interface equipment 128 can provide access to networks 108, using network components such as a packet-switched network interface card, a wireless transceiver, or a telephone network interface, for example, which may be present in a given computer system. Virtualizations of networking interface equipment and other network components such as switches or routers or firewalls may also be present, e.g., in a software-defined network or a sandboxed or other secure cloud computing environment. In some embodiments, one or more computers are partially or fully "air gapped" by reason of being disconnected or only intermittently connected to another networked device or remote cloud. In particular, functionality described herein could be installed on an air gapped network and then be updated periodically or on occasion using removable media 114. A given embodiment may also communicate technical data and/or technical instructions through direct memory access, removable or non-removable volatile or nonvolatile storage media, or other information storage-retrieval and/or transmission approaches.

One of skill will appreciate that the foregoing aspects and other aspects presented herein under "Operating Environments" may form part of a given embodiment. This document's headings are not intended to provide a strict classification of features into embodiment and non-embodiment feature sets.

One or more items are shown in outline form in the Figures, or listed inside parentheses, to emphasize that they are not necessarily part of the illustrated operating environment or all embodiments, but may interoperate with items in the operating environment or some embodiments as discussed herein. It does not follow that any items which are not in outline or parenthetical form are necessarily required, in any Figure or any embodiment. In particular, FIG. 11 is provided for convenience; inclusion of an item in FIG. 11 does not imply that the item, or the described use of the item, was known prior to the current innovations.

Technical processes shown in the Figures or otherwise disclosed will be performed automatically, unless otherwise indicated. No process contemplated as innovative herein is entirely manual or purely mental; none of the claimed processes can be performed solely in a human mind or on paper. Any claim interpretation to the contrary is squarely at odds with the present disclosure.

In a given embodiment zero or more illustrated steps of a process may be repeated, perhaps with different parameters or data to operate on. Steps in an embodiment may also be done in a different order than the top-to-bottom order that is laid out in the Figures. Arrows in method or data flow figures indicate allowable flows; arrows pointing in more than one direction thus indicate that flow may proceed in more than one direction. Steps may be performed serially, in a partially overlapping manner, or fully in parallel within a given flow. The order in which flowchart action items are traversed to indicate the steps performed during a process may vary from one performance of the process to another performance of the process. The flowchart traversal order may also vary from one process embodiment to another process embodiment. Steps may also be omitted, combined, renamed, regrouped, be performed on one or more machines, or otherwise depart from the illustrated flow, provided that the process performed is operable and conforms to at least one claim.

Some embodiments include a configured computer-readable storage medium 112. Storage medium 112 may include disks (magnetic, optical, or otherwise), RAM, EEPROMS or other ROMs, and/or other configurable memory, including in particular computer-readable storage media (which are not mere propagated signals). The storage medium which is configured may be in particular a removable storage medium 114 such as a CD, DVD, or flash memory. A general-purpose memory, which may be removable or not, and may be volatile or not, can be configured into an embodiment using items noted herein, in the form of data 118 and instructions 116, read from a removable storage medium 114 and/or another source such as a network connection, to form a configured storage medium. The configured storage medium 112 is capable of causing a computer system 102 to perform technical process steps for health management and guidance instruction issuance assistance, as disclosed herein. The Figures thus help illustrate configured storage media embodiments and process (a.k.a. method) embodiments, as well as system and process embodiments. In particular, any of the process steps illustrated in the Figures, or otherwise taught herein, may be used to help configure a storage medium to form a configured storage medium embodiment.

One of skill will recognize that not every part of this disclosure, or any particular details therein, are necessarily required to satisfy legal criteria such as enablement, written description, or best mode. Any apparent conflict with any other patent disclosure, even from the owner of the present innovations, has no role in interpreting the claims presented in this patent disclosure.

More generally, one of skill will recognize that not every part of this disclosure, or any particular details therein, are necessarily required to satisfy legal criteria such as enablement, written description, or best mode. Also, embodiments are not limited to the particular scenarios, motivating examples, operating environments, peripherals, software process flows, identifiers, data structures, data selections, naming conventions, notations, control flows, or other implementation choices described herein. Any apparent conflict with any other patent disclosure, even from the owner of the present innovations, has no role in interpreting the claims presented in this patent disclosure.

Different embodiments may provide different technical benefits or other advantages in different circumstances, but one of skill informed by the teachings herein will acknowledge that particular technical advantages will likely follow from particular innovation features or feature combinations.

The meaning of terms is clarified in this disclosure, so the claims should be read with careful attention to these clarifications. Specific examples are given, but those of skill in the relevant art(s) will understand that other examples may also fall within the meaning of the terms used, and within the scope of one or more claims. Terms do not necessarily have the same meaning here that they have in general usage (particularly in non-technical usage), or in the usage of a particular industry, or in a particular dictionary or set of dictionaries. Reference numerals may be used with various phrasings, to help show the breadth of a term. Omission of a reference numeral from a given piece of text does not necessarily mean that the content of a Figure is not being discussed by the text. The inventors assert and exercise the right to specific and chosen lexicography. Quoted terms are being defined explicitly, but a term may also be defined implicitly without using quotation marks. Terms may be defined, either explicitly or implicitly, here in the Detailed Description and/or elsewhere in the application file.

A "processor" is a thread-processing unit, such as a core in a simultaneous multithreading implementation. A processor includes hardware. A given chip may hold one or more processors. Processors may be general purpose, or they may be tailored for specific uses such as vector processing, graphics processing, signal processing, floating-point arithmetic processing, encryption, I/O processing, machine learning, and so on.

For the purposes of United States law and practice, use of the word "step" herein, in the claims or elsewhere, is not intended to invoke means-plus-function, step-plus-function, or United State Code Section 112 Sixth Paragraph/Section 112(f) claim interpretation. Any presumption to that effect is hereby explicitly rebutted.

In the present specification, reference to a "means" should be understood as referring to at least one processor 110 in operable electronic communication with at least one memory 112 configured with software (e.g., instructions 116) which controls execution of the processor to perform the indicated operations. Thus, an "identification information registration means for inputting identification information data of users who receive services" involves a memory 112, a processor 110, and instructions 116 which control the processor 110 and use the memory 112 as needed to input identification information data of users who receive services. Other kinds of means discussed herein are to be similarly understood.

For the purposes of United States law and practice, the claims are not intended to invoke means-plus-function interpretation unless they use the phrase "means for". Claim language intended to be interpreted as means-plus-function language, if any, will expressly recite that intention by using the phrase "means for". When means-plus-function interpretation applies, whether by use of "means for" and/or by a court's legal construction of claim language, the means recited in the specification for a given noun or a given verb should be understood to be linked to the claim language and linked together herein by virtue of any of the following: appearance within the same block in a block diagram of the figures, denotation by the same or a similar name, denotation by the same reference numeral, a functional relationship depicted in any of the figures, a functional relationship noted in the present disclosure's text. For example, if a claim limitation recited a "zac widget" and that claim limitation became subject to means-plus-function interpretation, then at a minimum all structures identified anywhere in the specification in any figure block, paragraph, or example mentioning "zac widget", or tied together by any reference numeral assigned to a zac widget, or disclosed as having a functional relationship with the structure or operation of a zac widget, would be deemed part of the structures identified in the application for zac widgets and would help define the set of equivalents for zac widget structures.

Whenever reference is made to data or instructions, it is understood that these items configure a computer-readable memory and/or computer-readable storage medium, thereby transforming it to a particular article, as opposed to simply existing on paper, in a person's mind, or as a mere signal being propagated on a wire, for example. For the purposes of patent protection in the United States, a memory or other computer-readable storage medium is not a propagating signal or a carrier wave or mere energy outside the scope of patentable subject matter under United States Patent and Trademark Office (USPTO) interpretation of the In re *Nuijten* case. No claim covers a signal per se or mere energy in the United States, and any claim interpretation that asserts otherwise in view of the present disclosure is unreasonable on its face. Unless expressly stated otherwise in a claim granted outside the United States, a claim does not cover a signal per se or mere energy.

Moreover, notwithstanding anything apparently to the contrary elsewhere herein, a clear distinction is to be understood between (a) computer readable storage media and computer readable memory, on the one hand, and (b) transmission media, also referred to as signal media, on the other hand. A transmission medium is a propagating signal or a carrier wave computer readable medium. By contrast, computer readable storage media and computer readable memory are not propagating signal or carrier wave computer readable media. Unless expressly stated otherwise in the claim, "computer readable medium" means a computer readable storage medium, not a propagating signal per se and not mere energy.

Although particular embodiments are expressly illustrated and described herein as processes, as configured storage media, or as systems, it will be appreciated that discussion of one type of embodiment also generally extends to other embodiment types. For instance, the descriptions of processes in connection with the Figures also help describe configured storage media, and help describe the technical effects and operation of systems and manufactures like those discussed in connection with other Figures. It does not follow that any limitations from one embodiment are necessarily read into another. In particular, processes are not necessarily limited to the data structures and arrangements presented while discussing systems or manufactures such as configured memories.

Reference herein to an embodiment having some feature X and reference elsewhere herein to an embodiment having some feature Y does not exclude from this disclosure embodiments which have both feature X and feature Y, unless such exclusion is expressly stated herein. All possible negative claim limitations are within the scope of this disclosure, in the sense that any feature which is stated to be part of an embodiment may also be expressly removed from inclusion in another embodiment, even if that specific exclusion is not given in any example herein. The term "embodiment" is merely used herein as a more convenient form of "process, system, article of manufacture, configured computer readable storage medium, and/or other example of the teachings herein as applied in a manner consistent with applicable law." Accordingly, a given "embodiment" may include any combination of features disclosed herein, provided the embodiment is consistent with at least one claim.

Not every item shown in the Figures need be present in every embodiment. Conversely, an embodiment may contain item(s) not shown expressly in the Figures. Although some possibilities are illustrated here in text and drawings by specific examples, embodiments may depart from these examples. For instance, specific technical effects or technical features of an example may be omitted, renamed, grouped differently, repeated, instantiated in hardware and/or software differently, or be a mix of effects or features appearing in two or more of the examples. Functionality shown at one location may also be provided at a different location in some embodiments; one of skill recognizes that functionality modules can be defined in various ways in a given implementation without necessarily omitting desired technical effects from the collection of interacting modules viewed as a whole. Distinct steps may be shown together in a single box in the Figures, due to space limitations or for convenience, but nonetheless be separately performable, e.g., one may be performed without the other in a given performance of a method.

Reference has been made to the figures throughout by reference numerals. Any apparent inconsistencies in the phrasing associated with a given reference numeral, in the figures or in the text, should be understood as simply broadening the scope of what is referenced by that numeral. Different instances of a given reference numeral may refer to different embodiments, even though the same reference numeral is used. Similarly, a given reference numeral may be used to refer to a verb, a noun, and/or to corresponding instances of each, e.g., a processor 110 may process 110 instructions by executing them.

As used herein, terms such as "a", "an", and "the" are inclusive of one or more of the indicated item or step. In particular, in the claims a reference to an item generally means at least one such item is present and a reference to a step means at least one instance of the step is performed. Similarly, "is" and other singular verb forms should be understood to encompass the possibility of "are" and other plural forms, when context permits, to avoid grammatical errors or misunderstandings.

Headings are for convenience only; information on a given topic may be found outside the section whose heading indicates that topic.

All claims and the abstract, as filed, are part of the specification. The abstract is provided for convenience and for compliance with patent office requirements; it is not a substitute for the claims and does not govern claim interpretation in the event of any apparent conflict with other parts of the specification. Similarly, the summary is provided for convenience and does not govern in the event of any conflict with the claims or with other parts of the specification. Claim interpretation shall be made in view of the specification as understood by one of skill in the art; innovators are not required to recite every nuance within the claims themselves as though no other disclosure was provided herein.

While exemplary embodiments have been shown in the drawings and described above, it will be apparent to those of ordinary skill in the art that numerous modifications can be made without departing from the principles and concepts set forth in the claims, and that such modifications need not encompass an entire abstract concept. Although the subject matter is described in language specific to structural features and/or procedural acts, it is to be understood that the subject matter defined in the appended claims is not necessarily limited to the specific technical features or acts described above the claims. It is not necessary for every means or aspect or technical effect identified in a given definition or example to be present or to be utilized in every embodiment. Rather, the specific features and acts and effects described are disclosed as examples for consideration when implementing the claims.

All changes which fall short of enveloping an entire abstract idea but come within the meaning and range of equivalency of the claims are to be embraced within their scope to the full extent permitted by law.

FURTHER EXAMPLES

Example 1. A health management system in which a service providing server, a doctor server, and a client terminal share information data via a network, including:

the client terminal which is provided with an identification information registration means for inputting identification information data of users who receive services, a medical interview information registration means for inputting medical interview information data, and an information transmission means for transmitting the input identification information data and medical interview information data to the service providing server; and the service providing server which is provided with a guidance instruction issuance request means for creating an issuance request data of guidance instruction regarding exercise prescription and nutrition prescription by a doctor based on the identification information data and the medical interview information data, and transmitting the issuance request data to the doctor server; and the doctor server which is provided with a guidance instruction automatic creation means for automatically creating guidance instruction data, a guidance instruction manual correction means for the doctor to modify the automatically created guidance instruction data, and a guidance instruction issuance means for transmitting guidance instruction data checked by the doctor to the service providing server and client terminal, based on the issuance request data obtained from the guidance instruction issuance request means.

Example 2. The health management system according to Example 1, wherein the service providing server further includes an interview information registration means for inputting interview information data based on the interview result between exercise or nutrition specialists and users, and wherein the information transmission means is used to send the interview information data to the doctor server, and wherein the guidance instruction manual correction means in the doctor server uses the received interview information data to correct the guidance instruction data.

Example 3. The health management system according to Example 1, wherein the system further includes a means for selecting a health improvement course tailored to the user, and wherein the guidance instruction automatic creation means automatically creates the guidance instruction data based on identification information data, medical interview information data, and a selected health improvement course.

Example 4. The health management system according to Example 1, wherein the service providing server further includes an exercise program automatic creation means for automatically creating an exercise program based on the guidance instruction data received from the doctor server and an exercise program manual correction means for making manual corrections as needed.

Example 5. The health management system according to Example 1, wherein the system further includes a wearable terminal that is connected to a network and can transmit and receive data, and wherein the wearable terminal is provided with a biometric information acquisition means for acquiring user biometric information data including pulse rate and step count, and wherein the information data can be shared among the service providing server, the doctor server and the client terminal through the network.

Example 6. The health management system according to Example 1, wherein the service providing server and the doctor server further provide an evaluation means for evaluating a health condition based on information data related to the user's exercise information, the user's nutritional information, or the user's biological information transmitted from the client terminal or the wearable terminal.

Example 7. The health management system according to Example 1, wherein the system is provided with a communication means capable of transmitting and receiving data by text message, voice call or video call between two or more of a client terminal, a service providing server and a doctor server.

Example 8. The health management system according to Example 7, wherein the communication means operates as a closed communication means except for the client terminal and the wearable terminal used by the user.

Example 9. The health management system according to Example 1, wherein the system further includes a user's family doctor terminal used by the user's family doctor and capable of transmitting and receiving data connected to the network, and the user's family doctor terminal is able to share the guidance instruction data checked by the doctor on exercise prescriptions and nutritional prescriptions.

Example 10. A device for assisting exercise prescription and nutrition prescription by a doctor, including:

an identification information registration means for inputting user identification information data; and a medical interview information registration means for inputting medical interview information data including lifestyle-related interviews; and a guidance instruction issuance request means for inputting the guidance instruction issuance request data regarding exercise prescription and nutrition prescription by the doctor based on the identification information data and the medical interview information data; and a guidance instruction automatic creation means for automatically creating guidance instruction data on exercise prescriptions and nutritional prescriptions, including exercise content and daily activity, based on information data acquired from the guidance instruction issuance request means; and a guidance instruction manual correction means for correcting the automatically created guidance instruction data with referring to the medical interview information data by the operation of the doctor who has specialized knowledge about lifestyle-related diseases, metabolic syndrome, and locomotive syndrome; and a guidance instruction issuance means for outputting the guidance instruction that has been checked by the doctor who has specialized knowledge about exercise prescriptions and nutrition prescriptions based on medical interview information data.

Example 11. The device according to Example 10, wherein the device further includes an interview information registration means for inputting interview information data based on an interview result between an exercise or nutrition specialist and a user, and the guidance instruction manual correction means uses the interview information data for correction.

Example 12. The device according to Example 10, wherein the device further includes a means for selecting a health improvement course suitable for the user, and the guidance instruction automatic creation means automatically creates guidance instruction data based on the identification information data, the medical interview information data and the selected health improvement course.

INDUSTRIAL APPLICABILITY

The present invention is useful as a system for preventing or ameliorating metabolic syndrome or locomotive syndrome.

DESCRIPTION OF SYMBOLS

1 Guidance instruction issuance assisting device
5 User terminal
5a Wearable terminal
6 Service providing server
7 Specialist doctor server
8 Internet
9 Family doctor terminal
10 Guidance instruction issuance means
11 Guidance instruction
11a User name display column
11b Course name display column
11c Specialist comment display column
11d Weight loss plan display column
11e Exercise prescription display column
11f Nutrition prescription display column
11g Issuer display column
12a Exercise program display column
12b Recommended meal menu display column 13 Text message
14a, 14b Comment
21 Identification information registration means
22 Medical interview information registration means
23 Information transmission means
25, 65, 75, 95 Communication means
31 Course selection means
32 Guidance instruction issuance request means
41 Guidance instruction automatic creation means
42 Guidance instruction manual correction means
50 User
51 Biometric information acquisition means
52, 92 Screen
60a Health exercise instructor
60b Registered dietitian
61 Interview information registration means
62 Exercise program creation means
63 Exercise program correction means
64, 74, 94 Evaluation means
66 Database
70 Specialist
90 Family doctor
100 Health management system
101 machine in a system 102, e.g., any device having at least a processor 110 and a memory 112 and also having a distinct identifier such as an IP address or a MAC (media access control) address; may be a physical machine or be a virtual machine implemented on physical hardware
102 computer system, also referred to as a "computational system" or "computing system", and when in a network may be referred to as a "node"
103 operating environment, also referred to as computing environment; includes one or more systems 102
104 users, e.g., user of an enhanced system taught herein; refers to a human or a human's online identity unless otherwise stated
106 peripheral device
108 network generally, including, e.g., LANs (local area networks), WANs (wide area networks), software-defined networks, clouds, and other wired or wireless networks
110 processor; includes hardware
112 computer-readable storage medium, e.g., RAM (random access memory), hard disks
114 removable configured computer-readable storage medium
116 instructions executable with processor; may be on removable storage media or in other memory (volatile or nonvolatile or both)
118 digital data in a system 102
120 kernel(s), e.g., operating system(s), BIOS (basic input/output system), UEFI (Unified Extensible Firmware Interface), device drivers
122 tools, e.g., version control systems, cybersecurity tools, software development tools, office productivity tools, social media tools, diagnostics, browsers, games, email and other communication tools, commands, and so on
124 user interface; hardware and software
126 display screens, also referred to as "displays"
128 computing hardware not otherwise associated with a reference number 106, 108, 110, 112, 114
130 cloud, cloud computing environment

What is claimed is:

1. A health management system in which a service providing server, a doctor server, and a client terminal securely share information data via a network, the health management system comprising:

the client terminal having a client terminal processor in communication with a client terminal memory which is configured with instructions which upon execution by the client terminal processor input identification information data of users who receive services, input medical interview information data, input interview information data of an interview result, and securely transmit the input identification information data and medical interview information data and interview information data to the service providing server, the client terminal processor tailored for encryption; and the service providing server having a service providing server processor in secure communication with a service providing server memory which is configured with instructions which upon execution by the service providing server processor create an issuance request data of guidance instruction regarding exercise prescription and nutrition prescription based on the identification information data and the medical interview information data and the interview information data, and securely transmit the issuance request data to the doctor server, the service providing server processor tailored for encryption;

the doctor server having a doctor server processor in secure communication with a doctor server memory which is configured with instructions which upon execution by the doctor server processor automatically create guidance instruction data, and securely transmit guidance instruction data to the service providing server and client terminal, based on the issuance request data, the doctor server processor tailored for encryption; and a wearable terminal that is connected to the network, and wherein the wearable terminal acquires biometric information data of users including pulse rate and step count, and wherein the biometric information data is securely shared among the service providing server, the doctor server and the client terminal through the network; and wherein the system securely transmits and securely receives medical or other health data by at least one of: text message, voice call, or video call.

2. The health management system according to claim 1, wherein the system further includes a user's family doctor terminal capable of transmitting and receiving data connected to the network, and the user's family doctor terminal is able to share the guidance instruction data.

3. The health management system according to claim 1, wherein the wearable terminal comprises an air-gapped computer.

4. The health management system according to claim 1, wherein the network comprises a software-defined network of a secure cloud computing environment.

5. The health management system according to claim 1, wherein the wearable terminal comprises a microphone.

6. The health management system according to claim 1, wherein the client terminal comprises a Field-Programmable Gate Array.

7. The health management system according to claim 1, wherein the client terminal comprises a System-on-a-Chip component.

8. The health management system according to claim 1, wherein the service providing server memory is configured with instructions which comprise code that runs on a virtual machine.

9. The health management system according to claim 1, wherein the client terminal memory is configured with instructions which comprise interpretable code.

10. The health management system according to claim 1, wherein the client terminal memory is configured with instructions which comprise machine code.

11. The health management system according to claim 1, wherein the health management system is configured with instructions which upon execution communicate technical data through direct memory access.

12. The health management system according to claim 1, wherein the health management system comprises a processor which is tailored for machine learning.

13. The health management system according to claim 1, wherein the health management system comprises a processor which is tailored for graphics processing.

14. The health management system according to claim 1, wherein the health management system comprises a processor which is tailored for floating-point arithmetic processing.

15. The health management system according to claim 1, wherein the health management system comprises a means for inputting identification information data of users.

16. The health management system according to claim 1, wherein the health management system comprises a means for inputting medical interview information data.

17. The health management system according to claim 1, wherein the health management system comprises a means for transmitting the input identification information data and medical interview information data to the service providing server.

18. The health management system according to claim 1, wherein the health management system comprises a means for creating the issuance request data of guidance instruction regarding exercise prescription and nutrition prescription by a doctor based on the identification information data and the medical interview information data.

19. The health management system according to claim 1, wherein the health management system is configured with instructions which upon execution communicate medical data using HTTPS.

20. The health management system according to claim 1, wherein the health management system comprises a voice command interface.

* * * * *